(12) United States Patent  (10) Patent No.: US 6,712,755 B2
Chang  (45) Date of Patent: Mar. 30, 2004

(54) LOCKING MECHANISM FOR AN ENDOSCOPIC OVERTUBE

(76) Inventor: Stanley F. Chang, 2723 W. Tenaya Way, Fresno, CA (US) 93711

( * ) Notice: Subject to any disclaimer, the term of this patent is extended or adjusted under 35 U.S.C. 154(b) by 0 days.

(21) Appl. No.: 10/099,299

(22) Filed: Mar. 15, 2002

(65) Prior Publication Data

US 2003/0187326 A1 Oct. 2, 2003

(51) Int. Cl.[7] ............................................. A61B 1/00
(52) U.S. Cl. ...................................... 600/114; 600/125
(58) Field of Search ............................. 600/114, 121, 600/125; 138/135, 158, 159, 162, 166, 167; 428/33, 36.9; 24/437–441; 606/1

(56) References Cited

U.S. PATENT DOCUMENTS

| | | | | |
|---|---|---|---|---|
| 3,530,898 A | * | 9/1970 | Wilson ........................ | 138/99 |
| 4,576,846 A | * | 3/1986 | Noel ........................ | 428/36.5 |
| 5,217,001 A | * | 6/1993 | Nakao et al. ................ | 600/123 |
| 5,259,366 A | * | 11/1993 | Reydel et al. ............... | 600/124 |
| 5,487,756 A | * | 1/1996 | Kallesoe et al. ............ | 607/118 |
| 5,779,624 A | * | 7/1998 | Chang ........................ | 600/114 |
| 5,941,815 A | * | 8/1999 | Chang ........................ | 600/114 |

* cited by examiner

*Primary Examiner*—John P. Leubecker
(74) *Attorney, Agent, or Firm*—Richard A. Ryan

(57) ABSTRACT

A locking mechanism for an endoscopic overtube comprising a generally tubular member having a slot extending from the distal end to the proximal end of the tubular member for insertion of an endoscope into the lumen configured to slidably receive the endoscope. The overtube has a second, smaller lumen configured to receive an elongated member. The slot has an interdigitating configuration with a plurality of interlocking members that join together to close the overtube. The second lumen connects the interlocking members to receive the elongated member therein to align and securely close the slot around the endoscope in the larger lumen. The elongated member in the second lumen connects the ends of the tubular member to keep the slot closed during an endoscopic procedure. A sleeve can be used at the distal end of the overtube to maintain closure of the slot.

16 Claims, 2 Drawing Sheets

LOCKING MECHANISM FOR AN ENDOSCOPIC OVERTUBE

BACKGROUND OF THE INVENTION

1. Field of the Invention

The field of the present invention relates to a locking mechanism to maintain three-dimensional closure of the longitudinal slot of a hollow tube, such as the type utilized in gastrointestinal endoscopy, especially colonoscopy. More specifically, the invention described herein is an improved locking mechanism that more securely and safely closes the slot so as to facilitate use of the slot for such procedures.

2. Background

As used herein, the terms "splint", "splinting device", and "overtube" are used interchangeably to refer to a generally elongated hollow tubular member that is adaptable for receiving a medical instrument, such as an endoscope. The term "endoscope" or "scope" is used to refer to a colonoscope, gastroscope, enteroscope, or other types of medical endoscopes. In referring to the opposite ends of the splint or scope, the "proximal end" refers to that part of the splint or scope which is closest to the control handle of the endoscope, and the "distal end" refers to that part of the splint or scope farthest from the control handle.

In gastrointestinal endoscopy, especially colonoscopy, straightness of the endoscope is necessary or desirable for advancement of the endoscope. Colonoscopy is the most sensitive and specific means for examining the colon, particularly for the diagnosis of colon cancers and polyps. Because the cecum, the portion of the colon furthest from the anus, is a common location for cancer, it is important that the entire colon be completely examined. However, because the anatomy of the colon can extremely vary from person to person, the technique of total colonoscopy is technically demanding. During a colonoscopy, the scope is inserted in the anus, through the rectum, sigmoid colon, descending colon, transverse colon, ascending colon and then into the cecum. Advancing the scope, which is typically about 160 centimeters in length, can be difficult due to a loop in the sigmoid colon. Once the scope reaches the descending colon or transverse colon, this loop must be reduced by withdrawing the scope to a straightened position. Failure to straighten the loop in the sigmoid colon prior to continuing can cause enlargement of the loop and result in pain and damage, including adverse cardiac reactions such as hypotension and bradycardia. Once the loop is straightened, further advancement of the endoscope can usually be accomplished.

In not so uncommon circumstances, however, the sigmoid loop often has a tendency to reform upon readvancement of the endoscope. When this happens, a sigmoid splint, or overtube, can be useful in preventing reformation of the sigmoid loop and facilitate advancement of the scope to the cecum. As is well known, however, when the need for a sigmoid splint arises, the tip of the scope is usually already in the descending or transverse colon. At this point, the colonoscopist may opt to remove the scope entirely in order to load the endoscope inside the sigmoid splint, in an end-to-end fashion, onto the scope, and start the procedure over again. A more convenient way, however, is to be able to do so without having to remove the scope from the patient. This is typically done by using a splint with a longitudinal slot along the entire length of the splint. The splint is loaded onto the endoscope in a side-to-side fashion by opening the slot, such that the scope does not have to be removed from the patient. Once seated around the scope, the slot is closed. The slot will then need to be secured in the closed position. A fastening or locking mechanism is needed to keep it closed in a secure fashion.

3. Related Art

A splinting tube with a straight longitudinal slot, which enables side-to-side loading onto the scope, is available (Olympus America, Inc., Melville, N.Y.). Its slot is a simple straight opening along the length of the splint. Once loaded onto the colonoscope, the slot is kept closed with one or more strips of adhesive tape. However, this fastening method is difficult because the adhesive tape, or part of it, may come off, especially when, as usual, there is lubricant on the splint and because even if it is securely taped, the tape fastens the slot only in two dimensions such that movement of the two edges against one another can still occur. Due to these limitations, the slotted splint described above is not widely utilized in endoscopic exams.

A different type of closure mechanism is described in U.S. Pat. No. 5,941,815 to Chang (the same inventor as of the present invention). In his patent, Chang describes a fastening mechanism using studs built onto one side of the slot, and receiving sockets on the other side of the slot. Closure of the slot is fastened by snapping these studs into the corresponding sockets. This fastening mechanism closes the slot in three dimensions. However, again, in the presence of lubricants, the fastened studs can still come off. Furthermore, the manufacturing process is very expensive. Another type of closure mechanism that has been disclosed is a zip-locking mechanism (i.e. similar to that used on plastic sandwich bags). However, the process of building a zip-locking mechanism into the wall of the splint is technically difficult, and the closure in the presence of lubricants still may not be very secure. If any bending of the splint occurs, and especially in the presence of lubricants, parts of the zip lock, along this approximately 40 cm length, can come apart.

What is needed is an improved securing mechanism for closing the longitudinal slot on splints used as an overtube for endoscopic procedures. Such an improved securing mechanism should provide a three-dimensional closure and alignment of the slot to securely fasten together and close the longitudinal slot. In addition, an improved securing mechanism should be unaffected by the presence of lubricants and bodily fluids. Ideally, such an improved securing mechanism should minimize the amount of labor and patient discomfort associated with utilizing a splint during an endoscopic procedure, such as a colonoscopy.

SUMMARY OF THE INVENTION

The locking mechanism for an endoscopic overtube of the present invention provides the benefits and solves the problems identified above. That is to say, the present invention discloses a highly secure fastening mechanism for splints having a longitudinal slot that provides three-dimiensional closure and alignment of the slot. The locking effect of the present invention is not affected by lubricants, which are almost always present in endoscopic procedures. To the best of the inventor's knowledge, this endoscopic splinting device and this method of closure of its slot has never been described before. The locking mechanism of the present invention simplifies use of the splint during endoscopic procedures and reduces the labor required for those procedures and the likely discomfort of the patient.

In one embodiment of the present invention, the closure mechanism for a splint comprises an overtube made of a elongated Cylindrical or tubular member having two lumens placed in parallel relationship to one another. The larger lumen is sized and configured to receive the endoscope. The smaller locking lumen is used for the slot locking/fastening mechanism of the present invention. The slot is created by cutting one wall of the splint along its length. The cutting pattern involves one side of the locking lumen for a short distance, then crossing the locking lumen, then the other side of the locking lumen for a short distance, then crossing back to the first side again. This pattern is repeated many times along the entire length of the tubing. The end result is a longitudinal slot with a zig-zag, sine-wave, saw-toothed, or another interdigitating configuration. When the slot is closed, the locking lumen is aligned and continuous again. The cutting process can be performed with the die-cutting process. More than one smaller lumen may be utilized, with the extra lumen(s) being used for other purposes. The entire splint can also be made with the molding process. In use, after loading the scope into the splint through the open slot, the slot is closed and the locking lumen realigned. The closure is next locked into position with a string, wire or other elongated member by threading it through the locking lumen. After the string is pulled taut and anchored against the splint, a secure closure of the slot is accomplished.

Accordingly, the primary objective of the present invention is to provide a closure mechanism for an endoscopic overtube having the features generally described above and more specifically described below in the detailed description.

It is also an important objective of the present invention to provide a closure mechanism for an endoscopic overtube that securely closes the longitudinal slot on the overtube to facilitate use of the overtube in endoscopic procedures.

It is also an important objective of the present invention to provide a closure mechanism for an endoscopic overtube that comprises a slot having a plurality of interlocking components that join together to securely close the slot.

It is also an important objective of the present invention to provide a closure mechanism for an endoscopic overtube having a plurality of interlocking components that join together to securely close the slot and a separate locking lumen that interacts with the interlocking components to maintain the secure closure of the slot.

It is also an important objective of the present invention to provide a closure mechanism for an endoscopic overtube slot that utilizes a string, wire or other elongated member inside a separate lumen to facilitate the secure locking of the slot.

The above and other objectives of the present invention are explained in greater detail by reference to the attached figures and description of the preferred embodiment which follows. As set forth herein, the present invention resides in the novel features of form, construction, mode of operation and combination of parts presently described and understood by the claims.

BRIEF DESCRIPTION OF THE DRAWINGS

In the drawings which illustrate the best modes presently contemplated for carrying out the present invention.

DETAILED DESCRIPTION OF THE PREFERRED EMBODIMENTS

Figure 1:
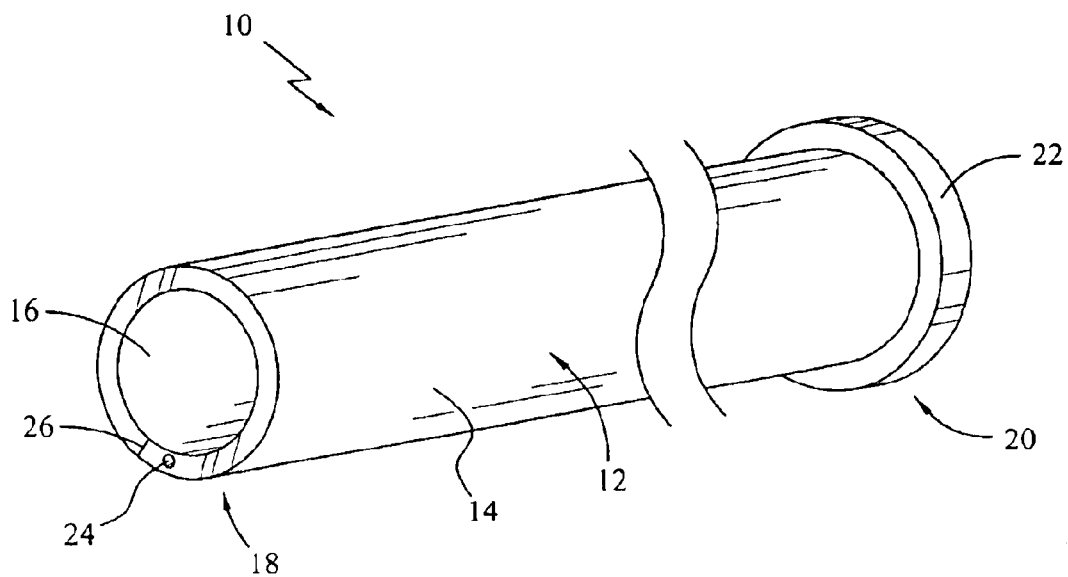
FIG. 1 is a top view of a splint utilizing the closure mechanism of the present invention showing the larger and smaller lumens.

With reference to the figures where like elements have been given like numerical designations to facilitate understanding of the present invention, and particularly with reference to the embodiments of the present invention illustrated in FIGS. 1 through 4, the secure slot closure mechanism of the present invention is suitable for use with an endoscopic overtube, designated generally as 10. The typical overtube 10 includes an elongated tubular member 12 with an outer surface 14 and an endoscope lumen 16 sized and configured to slidably receive an endoscope therein. Typically, the inside diameter of the endoscope lumen 16 is only slightly larger than the outside diameter of the endoscope to minimize the size of tubular member 12. Tubular member 12 has a distal end 18 which enters the human body and a proximal end 20 which can have an end section 22 having an outside diameter larger than the outside diameter of distal end 18 to prevent complete entry into the human body during the procedures described herein. Tubular member 12 can be shapes other than circular, for instance member 12 can be oval or any other shape that permits easy entry into and passage through the colon. The stiffness of splint 10 can vary along its length. For example, the distal end 18 can be more flexible than the remaining portion of the splint to facilitate easy insertion of overtube 10 into the human colon. Outer surface 14 of tubular member 12 can include a plurality of insertion markings (not shown) at spaced apart intervals to indicate the depth of insertion of tubular member 12 into the colon.

Overtube 10 can be made out of a variety of materials, including rubber, plastic, silicone and others (preferably a relatively soft material that will not damage the endoscope or the colon). Many of the preferred materials can be formed into the elongated tubular member 12 by use of an extrusion process. This same process, which forms endoscope lumen 16, can also be used to form a smaller locking lumen 24, best shown in FIGS. 1 and 2, that is positioned generally parallel to the endoscope lumen 16 from the distal end 18 to the proximal end 20. In the preferred embodiment, the shape of tubular member 12 is slightly ovoid or egg-shaped, as shown in the figures, and the locking lumen 16 is placed inside the thickened portion of the tubular body 12. As explained in more detail below, the locking lumen 24 is used in conjunction with the locking mechanism of the present invention to securely close a longitudinally oriented open-ended slot, shown as 26, in the overtube 10. Lumens 16 and 24 are shown in the figures as generally circular. However, either lume(n, particularly locking lumen 24, can be of other, non-circular shapes.

As is known in the art, slot 26 is sized to removably receive the endoscope into the endoscope lumen 16. Using slot 26, the endoscope does not have to be inserted or pre-loaded onto overtube 10 prior to inserting the endoscope into the patient. In use, after the scope is introduced into the descending colon or transverse colon of the patient, it is straightened in the usual fashion by reducing the sigmoid loop. Overtube 10 is then loaded onto the endoscope by opening slot 26. In the typical prior art, slot 26 is a straight cut into the overtube 10 and it is closed by sealing it with adhesive tape on the outer surface 14 of tubular member 12. As set forth below, an improved closure mechanism, shown generally as 28, can be utilized to provide a more secure and safer closure of the slot 26.

Figure 2:
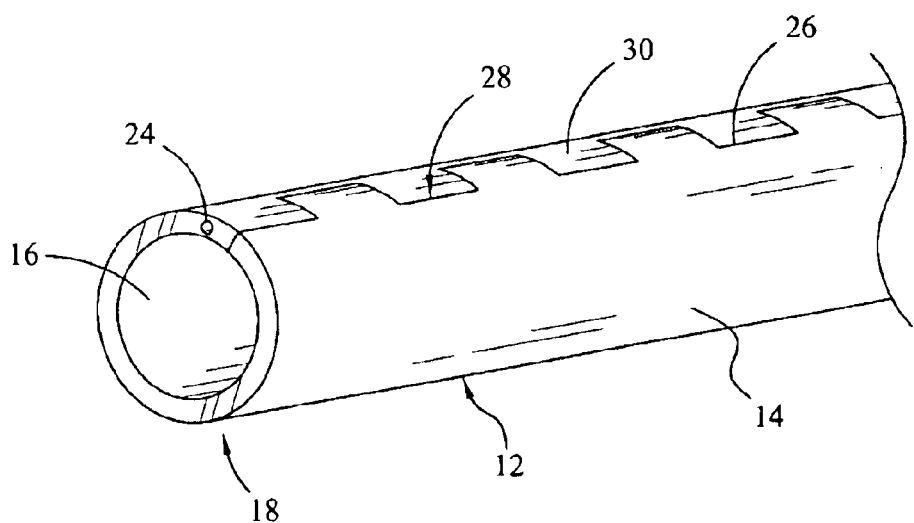
FIG. 2 is a bottom view of the splint of FIG. 1 showing the slot.
Figure 3:
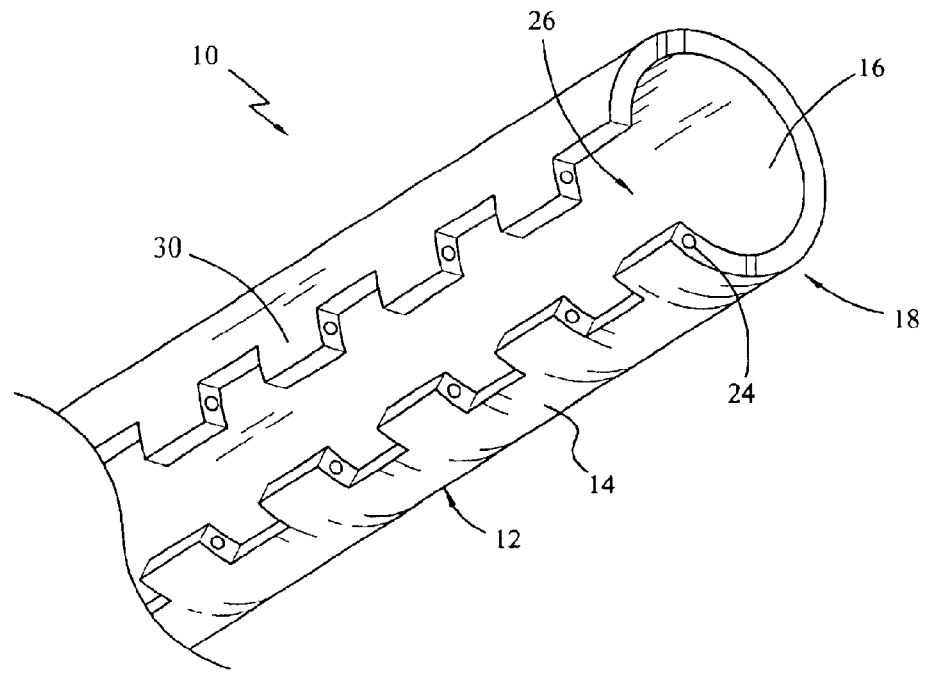
FIG. 3 is a bottom view of the splint of FIG. 1 showing the slot opened and the alignment of the smaller lumen disrupted.
Figure 4:
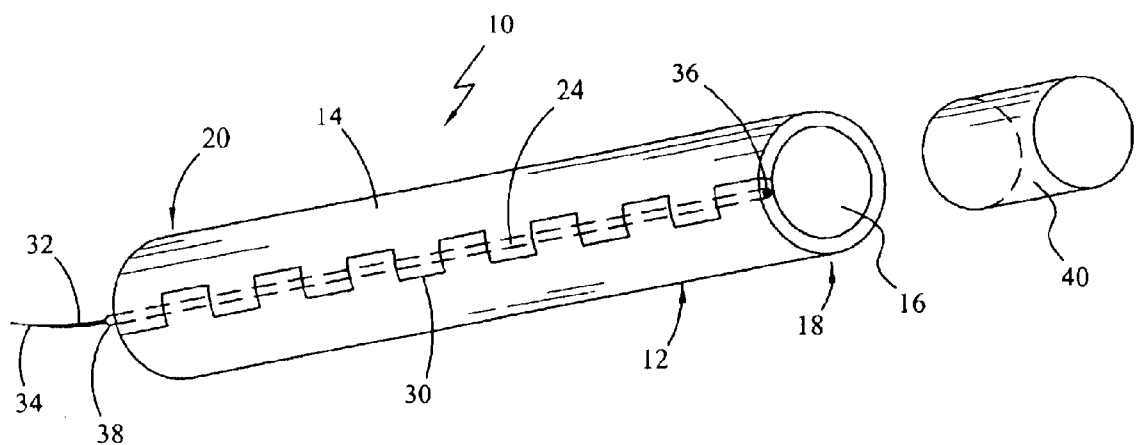
FIG. 4 is a bottom view of the splint of FIG. 1 showing the slot closed and locked closed with a string threaded through the smaller, locking lumen and a sleeve which can be used with the splint.

Instead of a straight slot 26, in the preferred embodiment of overtube 10, slot 26 is configured to accomplish the objectives set forth herein. The preferred configurations include a saw-toothed, zig-zag, sine-wave and other interdigitating configuration (FIGS. 2, 3 and 4 show a step-wave type of configuration). Other interdigitating configurations are also possible, for instance in cross-section, the apposing edges of the slot can have a V-shaped, W-shaped or curved configuration, with one edge being convex, and the other edge concave. In any such configuration, the closure mechanism 28 comprises a plurality of interlocking members 30 that join together. The locking lumen 24 passes through the individual interlocking members 30, as shown in FIGS. 3 and 4, when slot 26 is closed.

Although it is possible for overtube 10 to be configured such that the slot 26 to be securely closed by the action of the interlocking members 30 joining together, the preferred embodiment of the present invention utilizes a separate elongated member 32 to pass through the locking lumen 24 and interlocking members 30 so as to join the two sides of slot 26 securely together. Elongated member 32 can be a wire, string or the like that is either stiff or flexible, tubular or solid, that is capable of fitting in locking lumen 24 and passing through the interlocking members 30. In the preferred -configuration, elongated member 32 is a string or string-like member having some amount of elasticity to stretch between ends 18 and 20 of overtube 10. In this configuration, a stiffer guide wire 34 can used to assist the operator or physician in threading elongated member 32 through the locking lumen 24. Also in the preferred configuration, elongated member 32 can have a bulbous or button-like trailing end 36 that cannot pass into or through locking lumen 24 once the elongated member 32 is pulled taut and a fastener member 38 at or near the opposite end of elongated member 32 from trailing end 34 to hold elongated member 32 taut and slot 26 closed. Fastener member 38, such as an expanding clip (i.e., like a toggle bolt), can be integral with elongated member 32 and configured to pass through locking lumen 24 so it can open or otherwise expand once it exits locking lumen 24 at proximal end 20. Alternatively, fastener member 38 can be a separate member that is placed on elongated member 32 once it exits locking lumen 16 and is sufficiently extended therefrom to make elongated member 32 be taut inside locking lumen 16. Markings (not shown) can be placed on elongated member 32 where it exits the overtube 10 to assure continued proper positioning of the fastener 38 even when the overtube 10 is inside the colon.

In the preferred embodiment, the overtube 10 of the present invention utilizes a tubular sleeve 40, shown in FIG. 4, that is place over the distal end 18 of tubular member 12. The purpose of sleeve 40 is to reduce the likelihood that slot 26 at distal end 18 would "split" open during a colonoscopy. The possibility of the slot 26 inadvertently opening during colonoscopy is the greatest when the endoscope is inside the patient and is in a curved condition. Because the endoscope is not straight, or even substantially straight, the process of advancing overtube 10 over the endoscope requires overtube 10 to push against the endoscope in order to slide past the curved section. This pushing action could force open the closure mechanism 28. Preferably sleeve 40 has a relatively short length (i.e., 2 to 5 cm) to primarily cover the tip of overtube 10 at its distal end 18 and be made from a thin, flexible material, such as rubber, latex, silicone or other like materials. The inner diameter of sleeve 40 should be substantially equal to or slightly larger than the outside diameter of overtube 10 so that it tightly fits around the outside surface 14 of overtube 10 (for some materials, it may be sufficient that the inner diameter of sleeve 40 is less than the outer diameter of overtube 10). Sleeve should provide a tight fit around overtube 10. To remove sleeve 40, it can be cut off of overtube 10. Preferably, sleeve 40 is inexpensive so that it can be used only once and then discarded.

In use, when the advancement of the endoscope is prevented by the formation of a sigmoid loop or other reasons, the operator or physician will pull a portion of the endoscope out of the patient to reduce the sigmoid loop and then to place the overtube 10 around the endoscope. With slot 26, overtube is loaded by placing the endoscope lumen 16 around the endoscope in a side-to-side fashion through slot 26. Once the overtube 10 is loaded, slot 26 is closed. The elongated member 32 is pulled through the locking lumen 24 from the distal end 18 of the splint toward the proximal end 20 of the overture 10. In one embodiment, leading guide wire 34 is first fed through the locking lumen 24 until it reaches the other side, when it is then pulled through. The guide wire 34 and elongated member 32 are pulled through locking lumen 24 until the bulbous trailing end 36 abuts distal end 18 of overtube 10. Besides preventing elongated member 32 from being pulled through, it provides a mechanism by which elongated member 32 can be pulled taut. At the proximal end 20, an expanding fastener member 38 is pulled through locking lumen 24 and is secured against proximal end 20 by expanding fastener member 38. Alternatively, fastener member 38 can be placed on elongated member 32 where it exits overtube 10 to lock interlocking members 30 together and close slot 26. Thus, elongated member 32 pulled taut inside locking lumen 24 assures secure closure of slot 26.

To use sleeve 40, the endoscope should be preloaded (i.e., placed on the endoscope) with sleeve 40 so that when the endoscope is placed inside overtube 10, it can be slid to distal end 18 of overtube 10. Once overtube 10 is closed, preferably after closure mechanism 28 has securely closed slot 26, sleeve 40 is pulled over and onto the distal end 18 of overtube 10 to cover the outer surface 14 of overtube 10 at the distal end 18. Sleeve 40 will assist closure mechanism 28 in keeping slot 26 closed during the advancement of overtube 10 over the endoscope and during the colonoscopy procedure.

As shown, tubular member 12 can have a thicker wall where locking lumen 24 is located to improve the overall rigidity of overtube 10. Leading wire 36 and any excess part of elongated member 32 can be cut once elongated member 32 is pulled taut and slot 26 closed. Once the endoscopic procedure is completed, elongated member 32 can be cut and removed from either end 18 or 20 of overtube 10. The slot 26 is then opened and overtube 10 is removed from the endoscope.

While the above description contains many specifics, these should not be construed as limitations on the scope of the invention, but rather as an exemplification of one preferred embodiment thereof. Accordingly, the scope of the invention should be determined not by the embodiments illustrated, but by the appended claims and their legal equivalents.

What is claimed is:

1. An overtube for use with an endoscope, comprising:

a generally elongated tubular member having a proximal end, a distal end and an outer surface;

an endoscope lumen disposed in said tubular member, said endoscope lumen sized and configured to slidably receive the endoscope;

a locking lumen disposed in said tubular member, said locking lumen generally parallel to said endoscope lumen;

a slot disposed along said tubular member and interconnecting said endoscope lumen with said outer surface of said tubular member for receiving the endoscope into said endoscope lumen through said slot, said slot having an interdigitating configuration comprised of a plurality of interlocking members, said locking lumen passing through said interlocking members of said slot;

an elongated member sized and configured to be received in said locking lumen and securely align and maintain said slot in a closed position, said elongated member has a leading end and a trailing end, said leading end configured to fit through said locking lumen, said trailing end having a generally bulbous configuration to prevent passage of said trailing end into said locking lumen; and a fastener member at said leading end of said elongated member to fasten said elongated member against said proximal end of said tubular member.

2. The overtube of claim 1, wherein said slot is configured in a generally a step-wave configuration.

3. An overtube of claim 1 further comprising a sleeve sized and configured to tightly fit over said distal end of said tubular member.

4. An overtube for use with an endoscope, comprising:

a generally elongated tubular member having a proximal end, a distal end and an outer surface;

an endoscope lumen disposed in said tubular member, said endoscope lumen sized and configured to slidably receive the endoscope;

a locking lumen disposed in said tubular member, said locking lumen generally parallel to said endoscope lumen;

a slot disposed along said tubular member and interconnecting said endoscope lumen with said outer surface of said tubular member for receiving the endoscope into said endoscope lumen through said slot, said slot having an interdigitating configuration comprised of a plurality of interlocking members, said locking lumen passing through said interlocking members of said slot;

an elongated member sized and configured to be received in said locking lumen and securely align and maintain said slot in a closed position, said elongated member having a leading end and a trailing end, said leading end configured to fit through said flocking lumen, said trailing end having a generally bulbous configuration to prevent passage of said trailing end into said locking lumen; and a fastener member, said fastener member configured to attach to said leading end of said elongated member to fasten said elongated member against said proximal end of said tubular member.

5. The overtube of claim 4, wherein said slot is configured in a generally a step-wave configuration.

6. An overtube of claim 4 further comprising a sleeve sized and configured to tightly fit over said distal end of said tubular member.

7. A method of using an elongated overtube having opposing ends and a longitudinal slot with an interdigitating configuration made up of a plurality of interlocking members to perform a medical procedure in an area of the colon using an endoscope, comprising the steps of:

a) inserting the endoscope into the anus;

b) advancing the endoscope in the colon;

c) withdrawing the endoscope to reduce or straighten a loop in the colon;

d) loading the overtube onto the endoscope outside the anus by opening the slot of the overtube and placing the endoscope inside an endoscope lumen disposed in the overtube;

e) closing the slot;

f) threading an elongated member into and through the entire length of a locking lumen that interconnects the plurality of interlocking members in the slot to securely join together the interlocking members;

g) pulling the elongated member taut against the ends of the overtube;

h) inserting the overtube along the endoscope into the colon; and i) advancing the endoscope and overtube into the colon to perform the medical procedure.

8. The method of claim 7 further comprising the step of fastening a fastener member against one of the ends of the overtube to lock said elongated member in said locking lumen and securely close the slot after said threading step.

9. The method of claim 7 further comprising the step of cutting any excessive length of said elongated member extending beyond the ends of the overtube after said threading step.

10. The method of claim 7 further comprising the step of lubricating the overtube prior to said overtube inserting step.

11. The method of claim 7 further comprising the step of preloading a sleeve on the endoscope prior to said endoscope inserting step.

12. The method of claim 11 further comprising the step of placing the sleeve over a distal end of the tubular member after said slot closing step.

13. The method of claim 11 further comprising the step of placing the sleeve over a distal end of the tubular member after said step of pulling the elongated member taut against the ends of the overtube.

14. An overtube for use with an endoscope, comprising:

a generally elongated tubular member having a proximal end, a distal end and an outer surface;

an endoscope lumen disposed in said tubular member, said endoscope lumen sized and configured to slidably receive the endoscope;

a locking lumen disposed in said tubular member, said locking lumen generally parallel to said endoscope lumen;

a slot disposed along said tubular member and interconnecting said endoscope lumen with said outer surface of said tubular member for receiving the endoscope into said endoscope lumen through said slot, said slot having an interdigitating configuration comprised of a plurality of interlocking members, said locking lumen passing through said interlocking members of said slot;

an elongated member sized and configured to be received in said locking lumen and securely align and maintain said slot in a closed position; and a sleeve sized and configured to tightly fit over said distal end of said tubular member.

15. The overtube of claim 14, wherein said slot is configured in a generally a step-wave configuration.

16. The overtube of claims 14, wherein said elongated member has a leading end and a trailing end, said leading end configured to fit through said locking lumen, said trailing end having a generally bulbous configuration to prevent passage of said trailing end into said locking lumen.

* * * * *